US008644575B2

(12) United States Patent
Piper et al.

(10) Patent No.: US 8,644,575 B2
(45) Date of Patent: Feb. 4, 2014

(54) PROCESSING OF ABDOMINAL IMAGES

(75) Inventors: Jim Piper, Edinburgh (GB); Ian Poole, Edinburgh (GB)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 13/036,414

(22) Filed: Feb. 28, 2011

(65) Prior Publication Data

US 2012/0219197 A1 Aug. 30, 2012

(51) Int. Cl.
*G06K 9/00* (2006.01)

(52) U.S. Cl.
USPC .......................................... 382/131; 382/294

(58) Field of Classification Search
USPC .................................................. 382/131, 294
See application file for complete search history.

(56) References Cited

U.S. PATENT DOCUMENTS

| 7,724,943 | B2 * | 5/2010 | Khamene et al. | 382/154 |
| 7,840,050 | B2 * | 11/2010 | Ramamurthy et al. | 382/131 |
| 8,355,552 | B2 * | 1/2013 | Schwartz et al. | 382/131 |
| 8,411,950 | B2 * | 4/2013 | Akinyemi et al. | 382/173 |

OTHER PUBLICATIONS

Noterdaeme et al., "Contrast Enhanced Magnetic Resonance Imaging of the Liver", 2008, 30th Annual International IEEE EMBS Conference, 831-834.*

Martin J.K. Blomley, et al., "Liver Perfusion Studied with Ultrafast CT", Journal of Computer Assisted Tomography, vol. 19(3), 1995, pp. 424-433.

K.A. Miles, et al., "Perfusion CT: a worthwhile enhancement?", The British Journal of Radiology. vol. 76, Apr. 2003, pp. 220-231.

Ettore Squillaci, et al., "Perfusion-CT monitoring of cryo-ablated renal cells tumors", Journal of Experimental & Clinical Cancer Research, vol. 28:138, 2009, 11 pages.

Chaan S. Ng, et al., "Perfusion CT in Patients With Metastatic Renal Cell Carcinoma Treated With Interferon", American Journal of Roentgenology, vol. 194, Jan. 2010, pp. 166-171.

W. Wee, et al., "Methodology for visualization and perfusion analysis of 4D dynamic contrast-enhanced CT imaging", Proceedings of the XVI$^{th}$ ICCR, 2010, 4 pages.

(Continued)

*Primary Examiner* — Jason M Repko
*Assistant Examiner* — Katrina Fujita
(74) *Attorney, Agent, or Firm* — Oblon, Spivak, McClelland, Maier & Neustadt, L.L.P.

(57) ABSTRACT

According to one embodiment there is provided a computer-automated image processing method applied to a four-dimensional (4D) image data set of a patient's abdomen, e.g. by dynamic contrast enhanced computer-assisted tomography (DCE-CT). One of the three-dimensional (3D) scan images is taken to as the reference volume and the others as target volumes. Before registration between the 3D scan images, the image data set is partitioned into an abdominal cavity domain, containing the organs inside the abdominal wall, and an abdominal wall domain including the abdominal wall and externally adjacent skeletal features, such as the spine and ribs. Registration is then carried out separately on the two domains to obtain two warp fields which are then merged into a 4D image data set of the whole volume for further use, which may be to carry out perfusion measurements, to display and to store the registered 4D image data set.

9 Claims, 7 Drawing Sheets (56) References Cited

OTHER PUBLICATIONS

Guido Gerig, et al., "Semiautomated ROI Analysis in Dynamic MRI-Studies: Part I: Image Analysis Tools for Automatic Correction of Organ Displacements", IEEE Transactions on Medical Imaging, vol. 11, No. 2, Jun. 1992, pp. 221-232.

S.E. Yuksel, et al., "Automatic detection of renal rejection after kidney transplantation", International Congress Series, vol. 1281, 2005, pp. 773-778.

K. Passera, et al., "A Non-Linear Registration Method for DCE-MRI and DCE-CT Comparison in Bladder Tumors", ISBI, 2008, pp. 1095-1098.

Jun Masumoto, et al., "A similarity measure for nonrigid volume registration using known joint distribution of targeted tissue: Application to dynamic CT data of the liver", Medical Image Analysis, vol. 7, 2003, pp. 553-564.

Christine Tanner, et al., "Quantitative evaluation of free-form deformation registration for dynamic contrast-enhanced MR mammography", Medical Physics, vol. 34, No. 4, Apr. 2007, pp. 1221-1233.

William R. Crum, et al., "Information Theoretic Similarity Measures in Non-Rigid Registration", IPMI, 2003, 378-387.

X. Zhuang, et al., "Robust registration between cardiac MRI images and atlas for segmentation propagation", Society of Photo-Optical Instrumentation Engineers, vol. 6914, 2008, 11 pages.

Hyunjin Park, et al., "Construction of an Abdominal Probabilistic Atlas and its Application in Segmentation", IEEE Transactions on Medical Imaging, vol. 22, No. 4, Apr. 2003, pp. 483-492.

Florian A. Potra, et al., "Protein Image Alignment via Piecewise Affine Transformations", Journal of Computational Biology, vol. 13, No. 3, 2006, pp. 614-630.

Alain Pitiot, et al., "Piecewise affine registration of biological images for volume reconstruction", Medical Image Analysis, vol. 10, Jun. 2006, pp. 465-483.

\* cited by examiner

PROCESSING OF ABDOMINAL IMAGES

BACKGROUND OF THE INVENTION

Embodiments described herein relate generally to computer-automated image processing of time sequences of volume image data sets of the abdomen.

In the medical field, three-dimensional (3D) image data sets, i.e. volume image data sets, are collected by a variety of techniques—referred to as modalities in the field—including computer-assisted tomography (CT), magnetic resonance (MR), ultrasound and positron-emission-tomography (PET).

For a number of years, perfusion in abdominal organs has been measured using so-called four-dimensional (4D) dynamic contrast enhanced CT (DCE-CT). In outline, the following procedure is applied. A bolus of contrast agent is injected. Then typically between 10 and 25 CT scans are acquired at intervals of a few seconds. The relevant vasculature and organs are identified in each scan and their CT densities measured. Using a calibration curve, CT densities can be converted to contrast agent concentrations. The sequence of concentrations at each locus is plotted against time, providing a perfusion curve for the locus.

Figure 1:
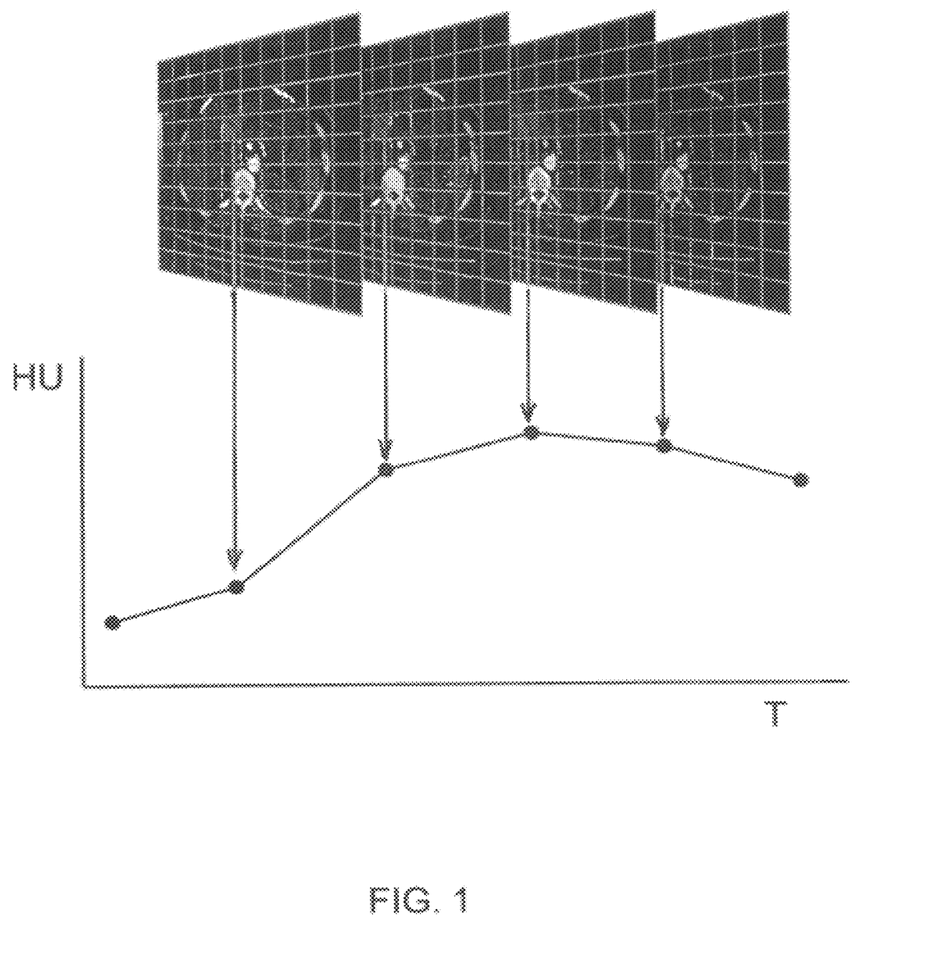
FIG. 1 is a graph of CT density in Houndsfield Units (HU) at a specific locus plotted against time during a 4D DCE-CT scan—a so-called perfusion curve.

FIG. 1 shows an example perfusion curve intensity in Houndsfield Units (HU), which is proportional to perfusion, against time (T). Each point on the curve is from the same locus in the patient as indicated by the arrows leading from the perspective 2D image panels.

Early work was based on time sequences of 2D slices, while more recently the advent of multi-slice scanners has enabled the rapid capture of time sequences of 3D CT volume images. The recent introduction of 320-slice CT scanners that can acquire high-resolution CT images with up to 16 cm axial extent in a single gantry revolution has made it feasible to capture multiple sequential images of entire organs such as the kidneys or the liver while delivering a relatively small total X-ray dose.

If the patient is completely immobile both externally and internally throughout the procedure, then the loci of interest need only be identified in a single scan, and can be automatically transferred to all other scans. Clearly, this greatly reduces the interaction time needed to generate the perfusion results. In reality, respiration-induced internal motion provides a significant challenge to the image processing. Two motion-reducing protocols are known. In one, the patient is instructed to hold their breath throughout the capture sequence. However, noting that patients are often sick, elderly, or both, a significant number fail to achieve this. Instead, at some point in the capture sequence they break the breath-hold with a deep gasping breath that results in major motion (often more than 30 mm) of the abdominal organs. An alternative protocol is to ask the patient to breath regularly but as shallowly or quietly as possible. In this case, the maximum extent of abdominal organ motion is reduced, at the expense of ubiquitous albeit smaller amounts of motion. Finally, not all patients even succeed in lying still on the CT table so that whole-body motions, usually in effect small rotations about the patient's longitudinal axis, are not unknown.

One rather unsatisfactory approach is simply to identify and ignore those volume images in which large organ motion is present. Automatic volume registration provides a better approach. Automatic registration has been widely used in DCE-CT and in the related field of DCE-MRI for almost two decades and is now available from a number of manufacturers as part of their perfusion analysis capabilities.

Respiration-induced motion affects the abdomen in a rather complex fashion. Put simply, the internal organs (liver, kidneys, spleen, pancreas, etc.) tend to move approximately axially (Z), driven by the downward motion of the diaphragm. Deep breathing can cause overall axial (Z) displacements of 30 mm or more, with smaller motion in the coronal (Y) direction and, usually, least motion in the sagittal (X) axis. In general the different organs will move by different amounts. For a patient in the usual prone position, the vertebrae and rear abdominal wall will remain approximately motionless. The front abdominal wall on the other hand tends to move mostly in the sagittal direction. The axial motion of the internal organs and the relatively immobile spine and abdominal wall have a boundary that is effectively discontinuous in places; the organs appear to "slide" along the inner surface of the abdominal wall. Finally, the organs are not themselves rigid but can subtly change in shape in addition to their overall gross movement.

BRIEF DESCRIPTION OF THE DRAWINGS

The invention is now described by way of example only with reference to the following drawings.

DETAILED DESCRIPTION

Figure 2:
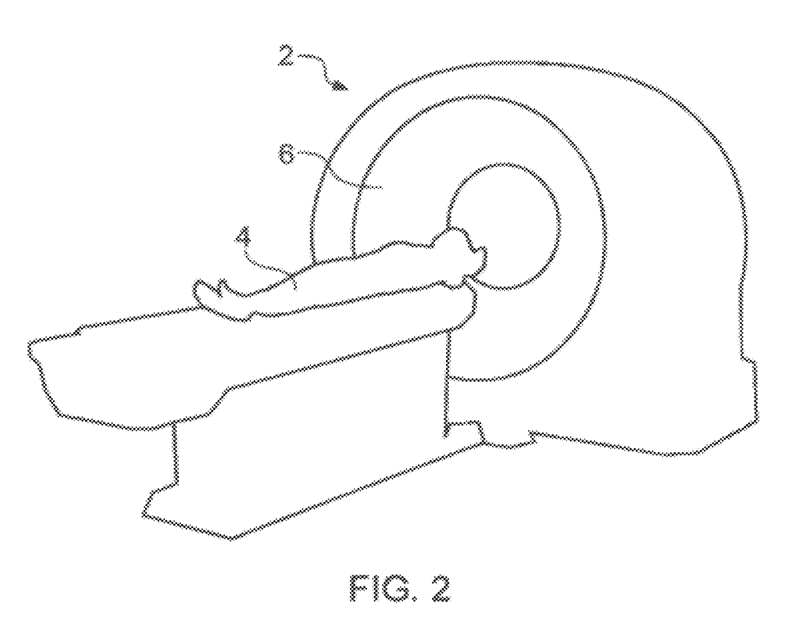
FIG. 2 shows a generic computer-assisted tomography (CT) scanner for generating volume data.

FIG. 2 is a schematic perspective view of a generic scanner 2, most especially a computer-assisted tomography (CT) scanner, for obtaining a 3D X-ray scan of a region of a patient 4. A patient's abdomen including one or more organs or other anatomical features of interest is placed within a circular opening 6 of the scanner 2. A series of image slices through the patient's abdomen is taken. Raw image data are derived from the scanner and could comprise a collection of one thousand 2D 512×512 data subsets, for example. These data subsets, each representing a slice of the region of the patient being studied, are combined to produce volume data. The volume data, which makes up a 3D image data set, comprise a collection of voxels each of which corresponds to a pixel in one of the slices. Thus the volume data are a 3D representation of the feature imaged and various user-selected 2D projections (output images) of the 3D representation can be displayed (typically on a computer monitor).

Different imaging modalities (e.g. CT, MR, PET, ultrasound) typically provide different image resolutions (i.e, voxel size), and the overall size of the volume imaged will further depend on the nature of the study. However, in the following description, by way of concrete example it will be assumed that the volume data comprise an array of 512×512×320 16-bit voxels arranged on a regular Cartesian grid defined by x-, y- and z-axes, with the voxels being spaced by 0.5 mm along each axis. This corresponds to an overall imaged volume of around 25 cm×25 cm×16 cm, which is more than adequate to encompass an abdominal organ of interest, such as a kidney, the liver, the bowel, the spleen or the pancreas. As is conventional, the volume data are aligned with transverse, sagittal and coronal planes. The xy-axes are in a transverse plane, the xz-axes are in a coronal plane and the yz-axes are in a sagittal plane.

Figure 3:
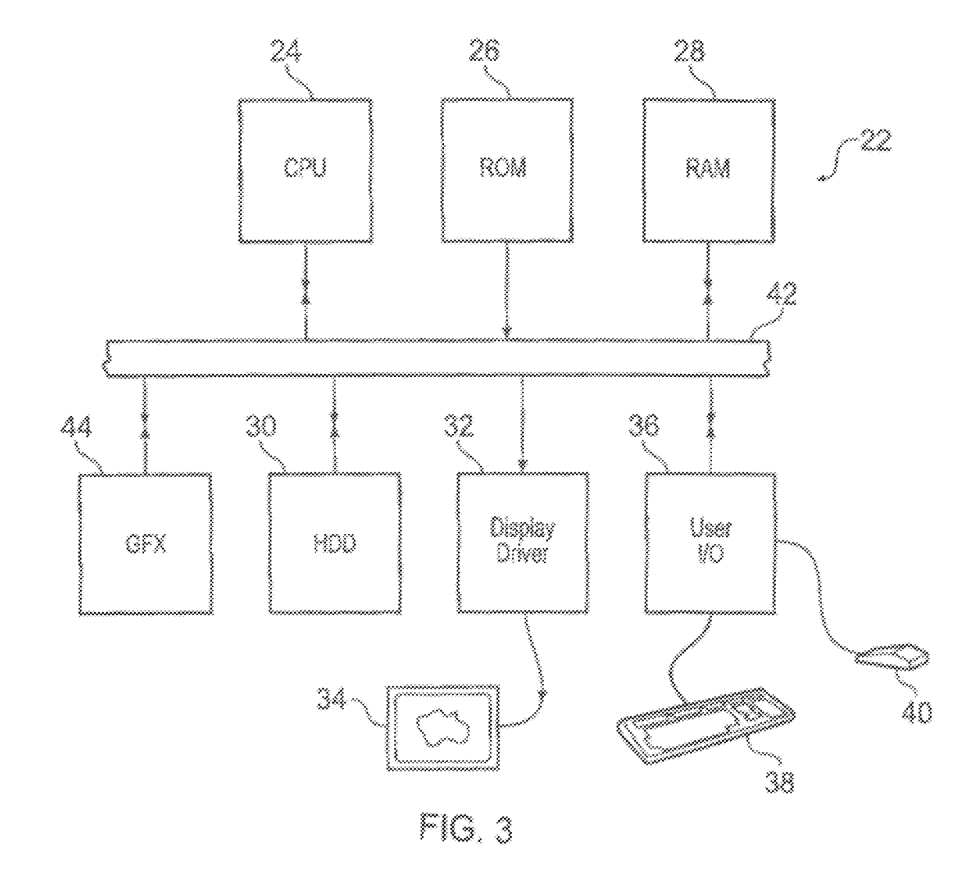
FIG. 3 schematically shows a computer for processing image data.

FIG. 3 schematically illustrates a general purpose computer system 22 configured to perform processing of volume data to generate two dimensional images. The computer 22 includes a central processing unit (CPU) 24, a read only memory (ROM) 26, a random access memory (RAM) 28, a hard disk drive 30, a display driver 32 and display 34 and a user input/output (IO) circuit 36 with a keyboard 38 and mouse 40. These devices are connected via a common bus 42. The computer 22 also includes a graphics card 44 connected via the common bus 42. In this example, the graphics card is a Radeon X800XT visual processing unit manufactured by ATI Technologies Inc., Ontario Canada. The graphics card includes a graphics processing unit (GPU) and random access memory tightly coupled to the GPU (GPU memory) (not shown in FIG. 3).

The CPU 24 may execute program instructions stored within the ROM 26, the RAM 28 or the hard disk drive 30 to carry out processing of signal values associated with voxels of volume data that may be stored within the RAM 28 or the hard disk drive 30. The RAM 28 and hard disk drive 30 are collectively referred to as the system memory. The GPU may also execute program instructions to carry out processing of volume data passed to it from the CPU.

Figure 4:
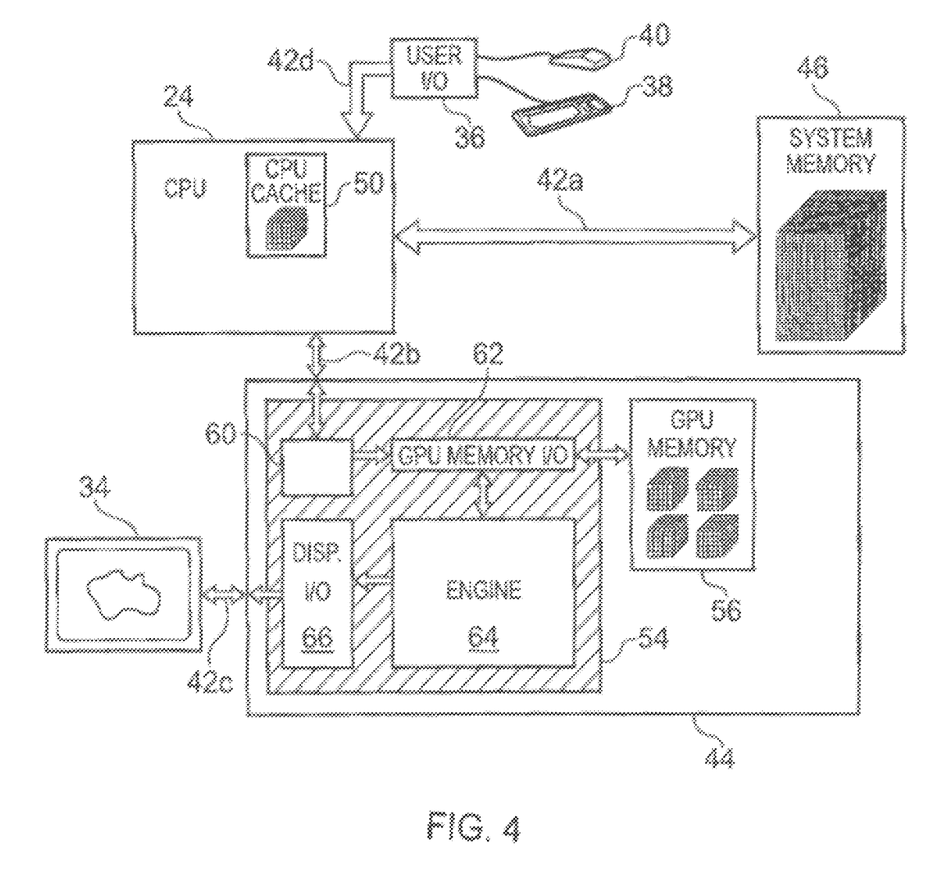
FIG. 4 schematically shows some of the features of the computer of FIG. 3 in more detail.

FIG. 4 schematically shows some of the features of the computer system shown in FIG. 3 in more detail. The RAM 28 and hard disk drive 30 are shown collectively as a system memory 46. Volume data 48 obtained from the scanner 2 shown in FIG. 2 is stored in the system memory as shown schematically in the figure.

Figure 5:
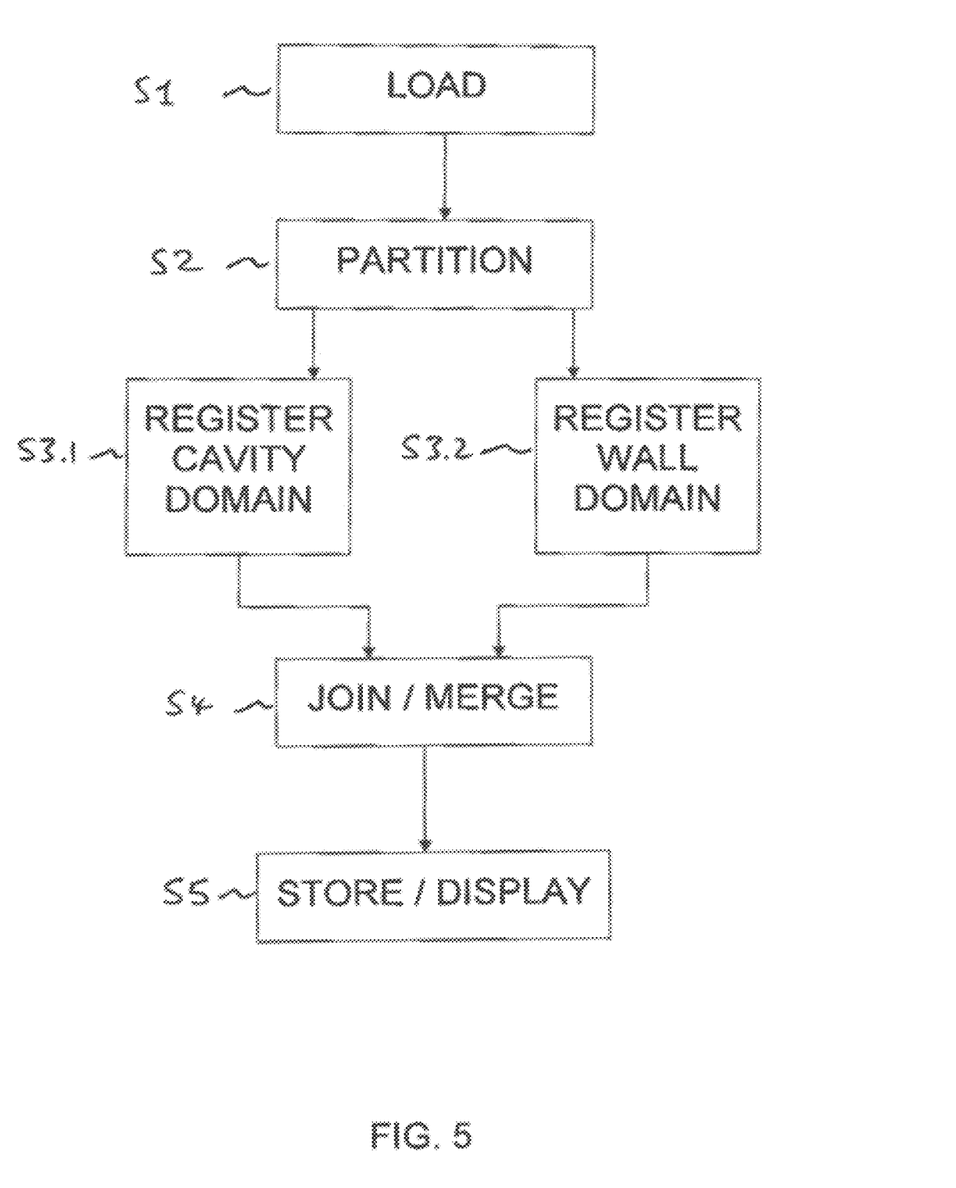
FIG. 5 is a flow diagram showing process steps of an image processing method.

To assist in showing the different data transfer routes between features of the computer system 22, the common bus 42 shown in FIG. 3 is schematically shown in FIG. 5 as a series of separate bus connections 42a-d. A first bus connection 42a connects between the system memory 46 and the CPU 24. A second bus connection 42b connects between the CPU 24 and the graphics card 44. A third bus connection 42c connects between the graphics card 44 and the display 34. A fourth bus connection 42d connects between the user I/O 36 and the CPU 24. The CPU includes a CPU cache 50. The graphics card 44 includes a GPU 54 and a GPU memory 56. The GPU 54 includes circuitry for providing an accelerated graphics processing interface 60, a GPU cache I/O controller 62, a processing engine 64 and a display I/O controller 66. The processing engine 64 is designed for optimized execution of the types of program instructions typically associated with processing 3D image data sets and carrying out 3D rendering of such data sets.

The user defines the required parameters using the keyboard 38 and mouse 40 in combination with a menu of options displayed on the display 34, for example using conventional techniques.

The example implementations of the invention described below relate to perfusion measurements on internal abdominal organs, such as the liver, either kidney, spleen or pancreas. The 3D image is obtained from a CT scan, i.e. 3D X-ray image. To provide contrast for the X-rays, the blood is typically dyed with a contrast agent having higher stopping power than the surrounding tissue. The patient is typically injected with a bolus of the contrast agent during an initial phase of the imaging process so that the earliest images taken are free of contrast agent effects, which then appear during the course of the image sequence. Iodine is a common contrast agent used for this purpose.

The following description presupposes that multiple 3D CT image data sets have been taken at short intervals from a patient using a suitable CT scanner, and is stored in system memory. Such data sets are sometimes referred to as 4D with the fourth dimension being time, or more specifically 4D dynamic contrast-enhanced CT (DCE-CT). Typically with 2011 technology, a few tens of CT scans, e.g. 10-30 scans, are acquired at intervals of a few seconds. The relevant vasculature and organs are identified in each scan and their CT densities measured. At least one initial scan in the sequence will be taken before injection of the contrast agent, or at least before the contrast agent can be expected to have reached the organ of interest, thereby to provide a suitable reference volume for registration without presence of the high stopping power contrast agent. In those scans where the contrast agent is present, using a calibration curve, CT densities in Houndsfield Units (HUs) can be converted to contrast agent concentrations. The sequence of concentrations at each locus is plotted against time then provides a perfusion curve for the locus.

The 4D DCE-CT data on which image processing methods as described herein were tested were collected as follows. The method was tested on 22 datasets each comprising a time-sequence of low-dose CT scans. The number of scans was in the range 10-30 with an average of 16 scans.

After bolus injection of the contrast agent, time sequences of 512×512×320 volume images were captured using a 320-detector row CT scanner (Aquilion ONE, Toshiba Medical Systems, Tochigi, Japan). The X-ray source setting was 80 kV, 210 mA, resulting in a relatively low total overall X-ray dose. The time sequence was: 10 scans at 3s intervals followed by a pause of 10s, then 3 scans at 7s intervals followed by a second pause of 10s, and then a 3 further scans again at an interval of 7s. The pixel spacing within slices varied somewhat from case to case, but was typically about 0.65 mm, while the slice spacing was 0.5 mm. Following CT reconstruction, the valid subset of each volume image consisted of a central cylinder of height approximately 11 cm, together with a conical region at each end that tapers from the radius of the cylinder to a point at the axial extremity of the volume, giving a total height of 16 cm, Pixels lying outside the valid subset were assigned a "padding" value to distinguish them from those having a valid CT value.

Images were produced using low X-ray doses and as a result were quite noisy following reconstruction. Noise was estimated by the following method. An image was first shifted by one pixel in the X direction, then subtracted from the original image. Assuming additive "white" noise, the standard deviation of the difference image divided by $\sqrt{2}$ is an estimate of the noise standard deviation. Noise standard deviation values in the order of 70 Hounsfield units (HU) were observed in most cases. For comparison, the intensity difference between a kidney and its adjacent fatty background is typically around 130 HU in a non-contrast scan, i.e. the signal to noise ratio is very low, in the order of two to one.

The method ensured that "padding" pixels lying outside the valid region of interest (ROI; the cylinder plus 2 cones, see above) had no impact on the registration. A 3D "abdomen domain" that included all of the body present in the scan but excluded surrounding air and the CT scanner table was found automatically by thresholding, choosing the largest connected component, and simplifying by a combination of binary image mathematical morphology operations. Pixels lying outside the abdomen domain were also excluded from consideration by the registration engine which is to be described in more detail further below.

In order to make perfusion measurements on internal abdominal organs (e.g. liver, kidney) it is necessary for an image processing method to be applied in order to register the multiple low-dose CT scans captured in a time sequence.

However, a straightforward approach of applying non-rigid registration to the complete volumes—whole volume non-rigid registration—does not perform well in all circumstances.

Whole volume non-rigid registration performs well if the data have been captured using a breath-hold protocol. However, it is clear from the results that some patients find it impossible to hold their breath for the requisite length of time, and movement artifacts appear in the images obtained by whole volume non-rigid registration. As an alternative to the breath-hold protocol, some data sets have been captured using a shallow-breathing protocol. Here the movement is less pronounced. However, movement artifacts are still seen in processed images that have been registered with whole volume non-rigid registration.

The main underlying issues are two-fold.

First, respiration causes the internal organs to move in the superior-inferior (axial) direction, by more than 30 mm in some cases, while the spine, rib-cage, pelvis and abdominal wall tend to move less, and predominantly in the anterior-posterior (coronal) direction.

Second, the requirement for the CT scans to be made with as low a dose as possible results in the scanned images having very high noise levels (noise standard deviations of more than 150 HU have been observed). High levels of image noise are known to degrade the performance of non-rigid registration.

An image processing method that performs better that a standard whole-volume registration approach is now described.

FIG. 5 shows the steps of the principal steps of the method which are as follows:

S1) Load: A 4D image data set made up of a time sequence of 3D image data sets is loaded onto a computer for processing, for example from a remote central file store of patient images.

S2) Partition: A pre-contrast 3D image data set is chosen to be the registration reference 3D image data set. The reference 3D image data set is processed by the computer to partition the abdomen into two regions, the "abdominal cavity" and the "abdominal wall plus adjacent skeletal features of the rib-cage, pelvis and spine". This is done fully-automatically by image analysis.

S3) Register: Each of the remaining 3D image data sets in the sequence is registered with the reference 3D image data set. The two regions in the reference 3D image data set are registered separately in sub-steps S3.1 and S3.2—in each case using rigid registration. In one example, non-rigid registration is carried out after rigid registration in this part of the process flow.

S4) Merge/Join: The resulting registrations are combined. In another example, if the non-rigid registration was not carried out as part of the registration step S3, it is carried out now after combining the registered sub-volumes.

S5) Store/Display: The combined registered 4D image data set is stored and/or displayed.

The automated partitioning method is now described in more detail with reference to an axial CT scan of the abdominal region.

1. Choose a volume that was obtained when the patient, or at least the patient's abdomen, did not contain any contrast agent. This is important because the skeleton is separated from the rest of the abdomen by intensity thresholding and the contrast agent by definition has high intensity which would interfere with this separation.
2. Apply a threshold in the order of 150 HU to the entire volume to segment the bones from almost all other tissue.
3. Apply several mathematical morphology operations to separate the spine. These are essentially standard, and are described in more detail below.
4. Using other mathematical morphology operations, find a first shell-like region containing ribs and/or pelvic bones (depending on the axial location of the scanned volume), as described in more detail below.
5. Apply a second threshold in the order of −600 HU to the entire volume to separate all tissue from the air background.
6. Find a second shell-like region by applying several mathematical morphology operations, as described in more detail below. The second shell-like region comprises the skin, subcutaneous fat and other exterior tissue that we refer to in this document as the "abdominal wall".

A suitable sequence of mathematical morphology operations to separate the spine is as follows:

Dilate the above-threshold region by a 2 mm spherical structuring element, and fill any internal holes, to join the vertebrae and fill any hollow bones.

Erode the resulting region by a 5 mm spherical structuring element. This will tend to separate the ribs from the spine.

Find the biggest connected component in the result of the previous step, and dilate it by a 5 mm spherical structuring element. This results in a slightly smoothed version of the spine.

Replace each 2D axial slice of the spine by its filled minimum enclosing convex polygon. This results in a smoother envelope for the spinal region. We refer to the result as the "spine domain".

Note that here and elsewhere in this document, "structuring element", "dilate", "erode", "open", "close" and "fill" are standard "mathematical morphology" terms and operations. "Domain" is a synonym of "mask". The text book Serra J., Image Analysis and Mathematical Morphology, 1982, ISBN 0126372403 provides details of mathematical morphology operations of the kind applied here, and is incorporated herein by reference in its entirety.

The mathematical morphology operations used to find the first shell-like region (ribs and/or pelvic bones) can be implemented as follows:

Take the cleaned-up above-threshold region found in the first dilation step mentioned above, and open using a 1 mm spherical structuring element.

Subtract the spine domain found above. The result comprises the ribs and/or pelvis.

Dilate the ribs/pelvis with a cylindrical structuring element of radius 5 mm and length (in the axial direction) 40 mm. This converts the ribs/pelvis to a shell-like "bone curtain domain" that is "hanging" in the axial direction.

Take the union of the bone curtain domain and the spine domain. This will usually comprise a single connected component that represents the bone region that is to be included as part of the abdominal wall rather than the abdominal cavity. This is referred to in the following as the "bone domain".

The mathematical morphology operations used to find the second shell-like region (skin, subcutaneous fat and other exterior tissue) is as follows in one example:

Find the largest connect component of the above-threshold region.

Replace each axial slice by the filled minimum enclosing convex polygon. This fills air gaps in the bowel, the bottom of the lungs, etc. and results in a "whole abdomen domain".

Take the complement of the whole abdomen domain, resulting in the region outside the body, including in particular the scanner table as well as the surrounding air. Dilate this region by 25 mm, with the result that it extends 25 mm into the body. The resulting domain now comprises the outside 25 mm shell of the body plus all of the exterior background, and is known as the "abdominal wall shell". (It will be appreciated that the choice of dimension may be varied as desired.)

Take the union of the bone domain and the abdominal wall shell, resulting in the "abdominal wall plus adjacent skeletal features of the rib-cage, pelvis and spine". Subtract this from the entire image volume. The result is the "abdominal cavity" domain. The abdominal wall and abdominal cavity are now disjoint and together comprise the entire volume.

Next the abdominal wall plus adjacent skeletal features, and the abdominal cavity, are made separate from each other by opening up a 15 mm wide space at their common boundary. In detail this can be achieved as follow: The abdominal cavity domain is first opened using a 15 mm spherical structuring element, thus smoothing its boundary by removing any small intrusions into the true abdominal wall. The final abdominal wall and bone domain is then constructed by dilating the abdominal cavity by 15 mm, then subtracting it from the whole abdomen domain found above.

The result is two domains, separated by a 15 mm-wide space, with smooth surfaces. The first comprises almost all of the abdominal internal organs (liver, kidney, spleen, pancreas, gall bladder, bowel); the second contains the spine, the ribs, the pelvis if present, everything between the skeleton and the skin, and most of the remaining abdominal wall (e.g. the anterior wall, which contains no bones).

Figure 6:
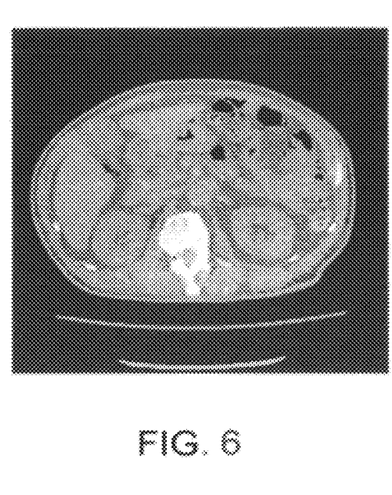
FIG. 6 is a 2D section volume rendered from a 3D CT scan of an abdomen.

FIG. 6 is a 2D volume rendered sectional view of a patient's abdomen taken by a CT scan, with no contrast agent present.

Figure 7:
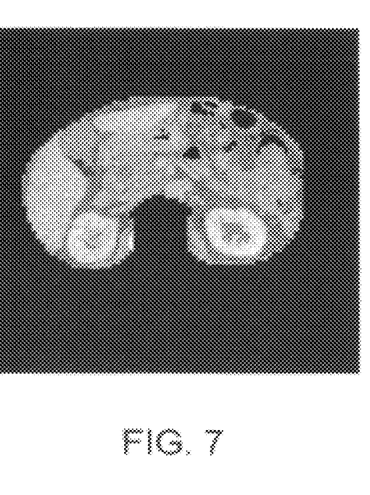
FIG. 7 shows a corresponding 2D section to FIG. 6 obtained from the same volume data set as FIG. 6 after the volume data set has been partitioned about the abdomen wall.

FIG. 7 is a corresponding image after partition has separated out the abdominal wall plus adjacent skeletal features domain, thereby only showing the abdominal cavity domain.

After completion of the partitioning, the subsequent steps are separate registration within each of the two domains or sub-volumes followed by joining or merging the resulting just-registered sub-volumes.

Registration is carried out to a reference volume separately to each of the two regions (abdominal cavity region and abdominal wall etc. region). Each of the two regions is represented by a "domain" or "mask" applied to the image volume chosen as the reference volume for registration. Each other perfusion-phase image volume (referred to hereinafter as the "target" volume) is then registered to the reference volume using only the portion of the reference volume contained within one domain. The registration comprises an initial "rigid" registration to take account of displacement, and optionally rotation to take account of any slight rotation between the target and reference, followed by non-rigid registration to accommodate soft-tissue distortions. In general, a registration process seeks to maximize a similarity measure between the reference image and the warped target or floating image. The similarity measure may be, for example, mutual information (MI) or normalized mutual information (NMI). A discussion of similarity measures can be found elsewhere in the literature, for example in the article Crum W. R., Hill D. L. G., Hawkes D. J. (2003) Information theoretic similarity measures in non-rigid registration. IPMI-2003, pp. 378-387 which is incorporated herein by reference in its entirety. The registration code was optimized for rapid execution on a modern multicore PC.

The result of the two separate registrations is two warp fields. Generally speaking, a warp field between two 3D data sets provides, for every voxel coordinate of the reference image, a relative offset to a corresponding location in the target or floating image. A warp field in Cartesian coordinates will thus comprise three orthogonal components, one for each of the 3 coordinate dimensions. The two warp fields in this case will be defined on two disjoint but closely adjacent domains: one for the abdominal cavity, and one for the abdominal wall etc.

One could simply combine the two warp-fields into one single warp field by extracting values from each within its own domain of definition, but this can potentially result in artifacts in the final combined image, such as gaps, tears, folds and occlusions.

Instead, it is better to erode the two domains until the subsets of the warp-fields defined on the eroded domains are consistent (i.e. no gaps, tears, folds, or occlusions), and then propagate the two warp-fields into the eroded regions in a consistent manner.

One specific way to implement this is a distance-transform-weighted propagation of the two warp-fields into the gap between the two domains, this being the 15 mm gap referred to earlier.

Another specific way, which is probably superior, is to use the method described above to merge the warp-fields obtained on the two domains from the rigid registration steps before applying non-rigid registration, and then apply non-rigid registration, seeded by the resulting warp-field, to the entire volume. This approach where the registration of the abdominal cavity is "blended" with the remainder of the abdomen can incorporate teachings from prior art on atlas-based segmentation in which individual organs or organ components are first rigidly registered, then the registrations are combined in a consistent manner to seed a non-rigid registration stage using approaches described in the literature, for example in the following two articles the contents of both of which are incorporated herein by reference in their entirety:

Zhuang X., Hawkes D. J., Crum W. R., Boubertakh R., Uribe S., Atkinson D., Batchelor P., Schaeffter T., Razavi R., Hill D. L. G. (2008) Robust registration between cardiac MRI images and atlas for segmentation propagation, SPIE Medical Imaging, vol. 6914, pp. 7

Park H., Bland P. H., Meyer C. R., Construction of an Abdominal Probabilistic Atlas and its Application in Segmentation, IEEE TRANSACTIONS ON MEDICAL IMAGING, VOL 22, NO. 4, APRIL 2003, pages 483-492

The person skilled in the art is familiar with techniques for merging warp fields so could use either of the above-mentioned ways or some other alternative way to achieve the merge.

The method has been fully implemented and tested on the 22 datasets referred to further above, each comprising an average of about 18 consecutive CT scans of the abdomen. A visual comparison shows that the method deals better with large motions of the internal organs than a whole-volume registration method, while being more or less indistinguishable from a whole-volume registration method when motion is small.

Methods described herein can be used within a hospital environment. In this case, the methods may usefully be integrated into a stand-alone software application, or with a Picture Archiving and Communication System (PACS). A PACS is a hospital-based computerized network which can store volume data representing diagnostic images of different types in a digital format organized in a single central archive. For example, images may be stored in the Digital Imaging and Communications in Medicine (DICOM) format. Each image has associated patient information such as the name and date of birth of the patient also stored in the archive. The archive is connected to a computer network provided with a number of workstations, so that users all around the hospital site can access and process patient data as needed. Additionally, users remote from the site may be permitted to access the archive over the Internet.

In the context of the present invention, therefore, a plurality of image volume data sets can be stored in a PACS archive, and a computer-implemented method of generating movies or other output images of a chosen one of the volume data sets according to embodiments of the invention can be provided on a workstation connected to the archive via a computer network. A user such as a radiologist, a consultant, or a researcher can thereby access any volume data set from the workstation, and generate and display movies or other images, such as a stills image of a heart feature at a particular phase of interest, using methods embodying the invention.

Figure 8:
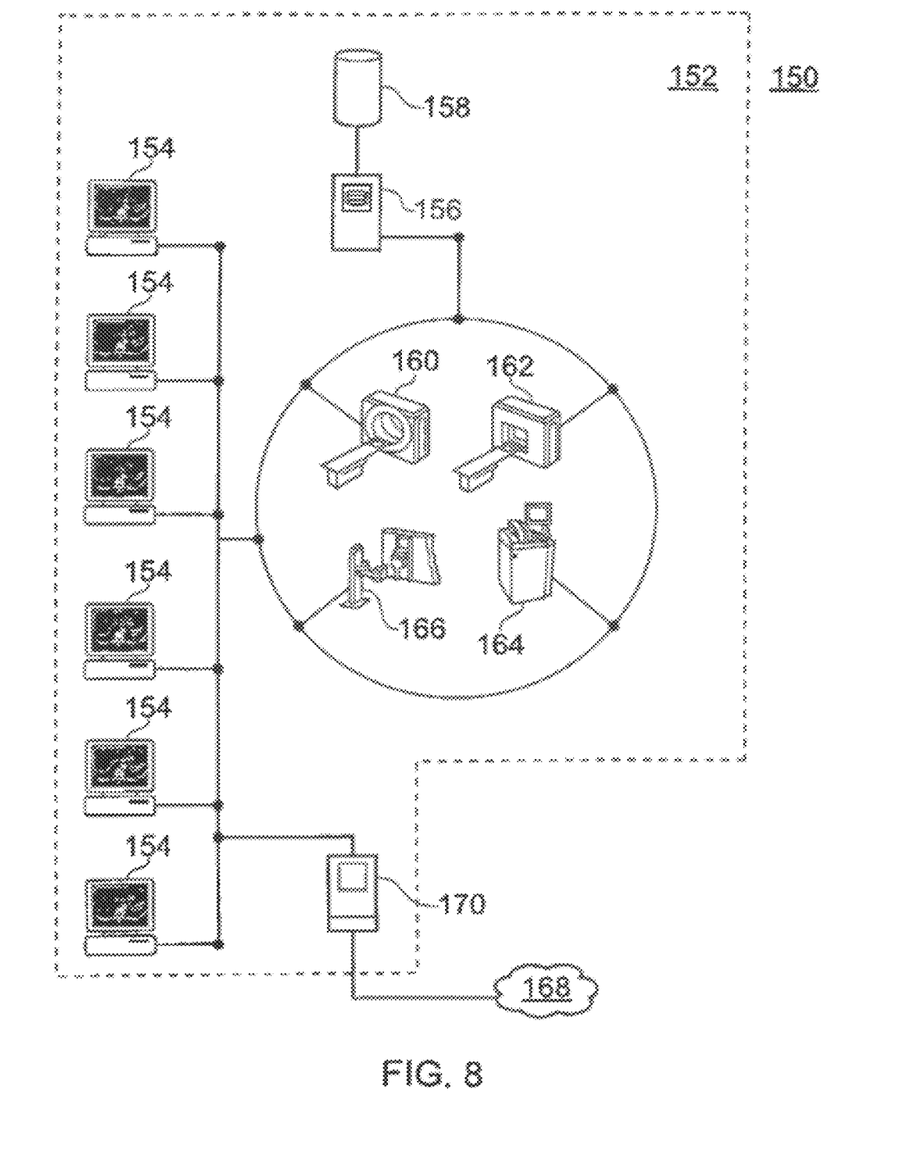
FIG. 8 shows an example computer network.

FIG. 8 shows an example computer network. The network 150 comprises a local area network in a hospital 152. The hospital 152 is equipped with a number of workstations 154 which each have access, via the local area network, to a hospital computer server 156 having an associated storage device 158. A PACS archive is stored on the storage device 158 so that data in the archive can be accessed from any of the workstations 154. One or more of the workstations 154 has access to a graphics card and to software for computer-implementation of methods described herein. The software may be stored locally at the or each workstation 154, or may be stored remotely and downloaded over the network 150 to a workstation 154 when needed. In other example, methods described herein may be executed on the computer server with the workstations 154 operating as terminals. For example, the workstations may be configured to receive user input defining a desired image data set and to display resulting images while volume rendering is performed elsewhere in the system. Also, a number of medical imaging devices 160, 162, 164, 166 are connected to the hospital computer server 156.

Image data collected with the devices 160, 162, 164, 166 can be stored directly into the PACS archive on the storage device 156. Thus patient images can be rendered and viewed immediately after the corresponding volume data are recorded, so that a swift diagnosis can be obtained in the event of medical emergency. The local area network is connected to the Internet 168 by a hospital Internet server 170, which allows remote access to the PACS archive. This is of use for remote accessing of the data and for transferring data between hospitals, for example, if a patient is moved, or to allow external research to be undertaken.

In the described embodiments, a computer implementation employing computer program code for storage on a data carrier or in memory can be used to control the operation of the CPU and GPU of the computer system. The computer program can be supplied on a suitable carrier medium, for example a storage medium such as solid state memory, magnetic, optical or magneto-optical disk or tape based media. Alternatively, it can be supplied on a transmission medium, for example a medium with a carrier such as a telephone, radio or optical channel.

A computer program product bearing machine readable instructions for carrying out the method is disclosed.

A computer loaded with and operable to execute machine readable instructions for carrying out the method is disclosed.

A computer program product is disclosed. Examples of a computer program product bearing machine readable instructions for carrying out the method described above are the mass storage device HDD 30 of FIG. 3, the ROM 26 of FIG. 3, the RAM 28 of FIG. 3 and the system memory 46 of FIG. 4, and the servers 156 or 170 of FIG. 8. Other forms of computer program product include a spinning disk based storage device such as a CD or DVD, or a USB flash memory device.

Examples of a computer loaded with and operable to execute machine readable instructions for carrying out the method described above are the computer of FIG. 3, the computer of FIG. 4, and individual elements, e.g. terminals 154 or collective multiple elements of the computer network system shown in FIG. 8, e.g. server 156 or 170 in combination with one or more of the terminals 154 or computers provided with the medical imaging devices 160, 162, 164 or 166.

Examples of a computer program product bearing machine readable instructions for carrying out the method described above are the mass storage device HDD 30 of FIG. 3, the ROM 26 of FIG. 3, the RAM 28 of FIG. 3 and the system memory 46 of FIG. 4, and the servers 156 or 170 of FIG. 8. Other forms of computer program product include a spinning disk based storage device such as a CD or DVD, or a USB flash memory device.

Embodiments of the invention may include incorporating the methods and associated computer programs described herein as a component in a volume rendering application.

While the method has been described with reference to 3D image data sets collected by computer-assisted tomography (CT) scanners, it is more generally applicable to imaging of other 3D and indeed 4D or higher dimensionality data sets obtained from a wide variety of image capture devices and a wide variety of objects.

For example, the method may be applied to a variety of imaging types used in the medical field, referred to as modalities. In particular, the methods described herein may be applied to 3D image data sets collected by computer-assisted tomography (CT) scanners, particularly the above-described DCE-CT, magnetic resonance (MR) scanners, particularly DCE-MRI, ultrasound scanners and positron-emission-tomography (PET) systems.

These 3D data sets are sometimes referred to as volume data. In medical imaging, 3D image data sets are generally large. Sizes of between 0.5 Gigabytes and 8 Gigabytes are not uncommon. For example, a medical image data set might comprise 1024×1024×320 16-bit voxels which corresponds to approximately 1 Gigabytes of data. From this an image comprising 1024×1024 16-bit pixels might be rendered.

In summary, the method thus involves separation of the abdominal cavity from the abdominal wall followed by separate registration of the two resulting sub-volumes.

More particularly a computer-automated image processing method has been described, comprising: (a) accessing (e.g. from a memory device such as the GPU memory 56, the system memory 46, the HDD 30, the hospital computer server 156 or its associated storage device 158) a 4D image data set comprising a plurality of 3D image data sets of a volume taken in time sequence, wherein the volume includes at least part of the abdomen of a living subject; (b) selecting (e.g. with instructions running on a processor such as the CPU 24 or the GPU 54) one of the 3D images to serve as a reference volume 3D image data set; (c) partitioning (e.g. with instructions running on a processor such as the CPU 24 or the GPU 54) the reference volume 3D image data set into an abdominal cavity domain inside the abdominal wall and an abdominal wall domain including the abdominal wall and externally adjacent anatomical features; (d) registering (e.g. with instructions running on a processor such as the CPU 24 or the GPU 54) each of the 3D image data sets to the reference volume 3D image data set for the abdominal cavity domain to obtain a first warp field defined over the abdominal cavity domain; (e) registering (e.g. with instructions running on a processor such as the CPU 24 or the GPU 54) each of the 3D image data sets to the reference volume 3D image data set for the abdominal wall domain to obtain a second warp field defined over the abdominal wall domain; (f) for each of the 3D image data sets, merging (e.g. with instructions running on a processor such as the CPU 24 or the GPU 54) the first and second warp fields into a single consistent merged warp field defined over the whole volume; and (g) using each of the merged warp fields to bring the corresponding 3D image data set into registration with the reference volume 3D image data set (e.g. with instructions running on a processor such as the CPU 24 or the GPU 54).

It has been further described how the first and second warp fields may be merged into the merged warp field by eroding the abdominal cavity domain with the abdominal wall domain until adjacent portions of the first and second warp fields are consistent, and then propagating the first and second warp fields into the eroded regions.

In some embodiments, the 4D image data set represents a study in which a contrast agent has been introduced to the subject, this being manifested by some, but not all, of the 3D image data sets having voxels affected by the contrast agent, and wherein the reference volume 3D image data set is selected to be a 3D image data set whose voxels are free of effects of the contrast agent. In particular, the study can be a perfusion study of an abdominal organ contained in the abdominal cavity domain.

While certain embodiments have been described, these embodiments have been presented by way of example only, and are not intended to limit the scope of the inventions. Indeed, the novel methods, computers and computer program products described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A computer-automated image processing method, comprising:
    accessing a 4D image data set comprising a plurality of 3D image data sets of a volume taken in time sequence, wherein the volume includes at least part of the abdomen of a living subject;
    selecting one of the 3D image data sets to serve as a reference volume 3D image data set;
    partitioning the reference volume 3D image data set into an abdominal cavity domain inside the abdominal wall and an abdominal wall domain including the abdominal wall and externally adjacent anatomical features;
    registering each of the 3D image data sets to the abdominal cavity domain of the reference volume 3D image data set to obtain a first warp field defined over the abdominal cavity domain without including a portion of the reference volume 3D image data set within the abdominal wall domain;
    registering each of the 3D image data sets to the abdominal wall domain of the reference volume 3D image data set to obtain a second warp field defined over the abdominal wall domain without including a portion of the reference volume 3D image data set within the abdominal cavity domain;
    for each of the 3D image data sets, merging the first and second warp fields into a single consistent merged warp field defined over the whole volume; and
    using each of the merged warp fields to bring the corresponding 3D image data set into registration with the reference volume 3D image data set.

2. The method of claim 1, wherein each of the first and second registrations comprises a rigid registration.

3. The method of claim 2, wherein the first registration further comprises a non-rigid registration after the rigid registration.

4. The method of claim 2, wherein a non-rigid registration is applied to the merged warp fields.

5. The method of claim 1, wherein the 4D image data set represents a study in which a contrast agent has been introduced to the subject, which is manifested by some, but not all, of the 3D image data sets having voxels affected by the contrast agent, and wherein the reference volume 3D image data set is selected to be a 3D image data set whose voxels are free of effects of the contrast agent.

6. The method of claim 5, wherein the study is a perfusion study of an abdominal organ contained in the abdominal cavity domain.

7. The method of claim 1, further comprising:
    volume rendering the processed 4D image data set into a sequence of 2D image data sets; and
    displaying the 2D image data sets in sequence to a user.

8. A non-transitory computer-readable medium storing machine readable instructions for carrying out the method of claim 1.

9. A computer loaded with and operable to execute machine readable instructions for carrying out the method of claim 1.

* * * * *